United States Patent [19]

Schmidt et al.

[11] Patent Number: 4,765,335
[45] Date of Patent: Aug. 23, 1988

[54] ANEURYSM CLIP

[75] Inventors: Ferenc J. Schmidt, Bryn Mawr, Pa.; P. Kevin Maughan, Sanibel, Fla.; Jack J. Guy, Sunnyvale, Calif.

[73] Assignee: Intermar, Inc., Upper Marlboro, Md.

[21] Appl. No.: 46,565

[22] Filed: May 6, 1987

Related U.S. Application Data

[63] Continuation-in-part of Ser. No. 26,266, Mar. 16, 1987, abandoned.

[51] Int. Cl.[4] .............................................. A61B 17/12
[52] U.S. Cl. ..................................... 128/326; 128/346; 24/545; 24/552
[58] Field of Search ............... 128/325, 326, 337, 346; 24/546, 547, 551, 552, 550, 549; 204/42

[56] References Cited

U.S. PATENT DOCUMENTS

| | | | |
|---|---|---|---|
| 3,207,679 | 9/1965 | Schmidt | 204/42 |
| 3,989,876 | 11/1976 | Moji et al. | 204/42 |
| 4,192,315 | 3/1980 | Hilzinger et al. | 128/346 |
| 4,316,780 | 2/1982 | Yoshida et al. | 204/42 |
| 4,340,061 | 7/1982 | Kees, Jr. et al. | 128/325 |
| 4,360,023 | 11/1982 | Sugita et al. | 128/325 |
| 4,375,391 | 3/1983 | Kushida et al. | 204/42 |
| 4,399,810 | 8/1983 | Samuels et al. | 128/337 |
| 4,407,285 | 10/1983 | Perlin | 128/325 |
| 4,430,169 | 2/1984 | Woods | 204/42 |
| 4,484,581 | 11/1984 | Martin et al. | 128/325 |
| 4,489,725 | 12/1984 | Casey et al. | 128/346 |
| 4,602,631 | 7/1986 | Funatsu | 128/325 |
| 4,606,796 | 8/1986 | Hanazima et al. | 204/42 |

Primary Examiner—Dalton L. Truluck
Assistant Examiner—Frank Wilkens
Attorney, Agent, or Firm—Charles W. Helzer

[57] ABSTRACT

An improved cerebral aneurysm clip fabricated from titanium or titanium alloys and utilizing a guide member consisting of a straight wire-like bridging guide secured across a U-shaped bend formed in one or both of the two cross arms of the aneurysm clip. The aneurysm clip is fabricated from a single, elongated resilient member of titanium or titanium alloy coiled at an intermediate portion to form a coil spring for normally urging the clamping arms of the clip together in a resilient manner. The clip further consists of two forearm sections extending outwardly and away from the coil spring in the direction of the clamping arms of the clip with the forearm sections terminating in inwardly bent first elbow portions that support respective cross arm sections. The cross arm sections extend from the respective first elbow portions in mutually crossing and slidably engaging relationship with each other and terminate in second inwardly bent elbow portions that support the respective clamping arms of the aneurysm clip. Because the clip is fabricated from titanium or titanium alloys, it can be readily color coded by a simple and safe electrolytic oxidation technique capable of providing a passivating oxide layer of different color for coding purposes for different sizes and shapes of clips being manufactured.

29 Claims, 2 Drawing Sheets

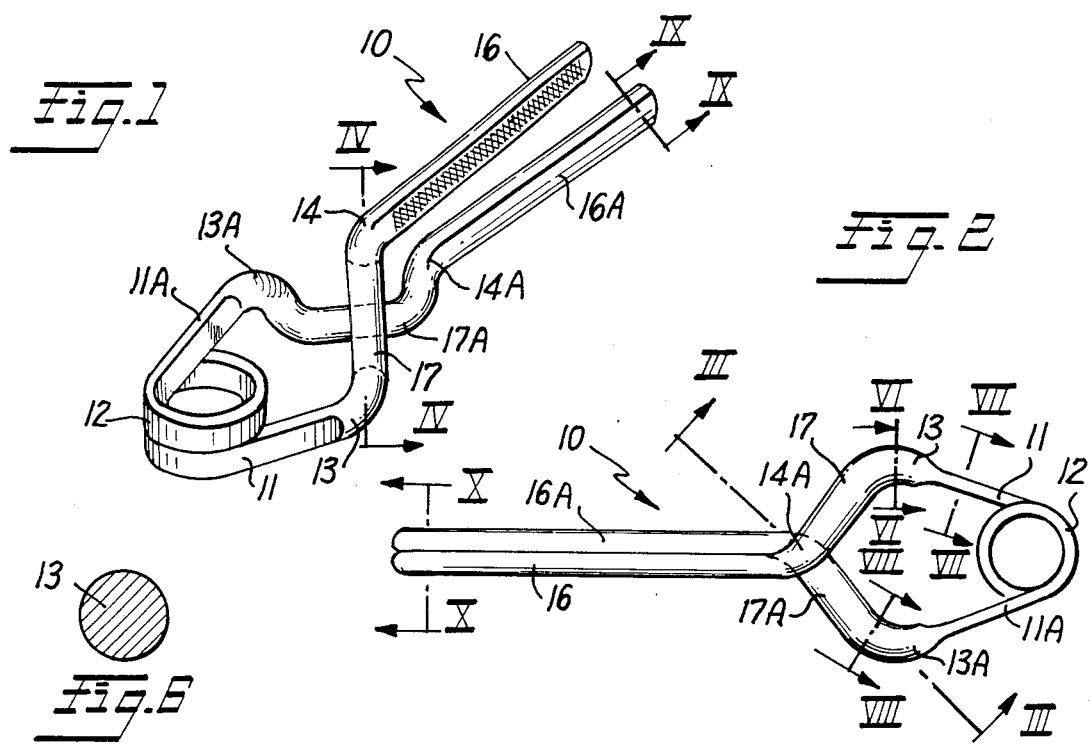
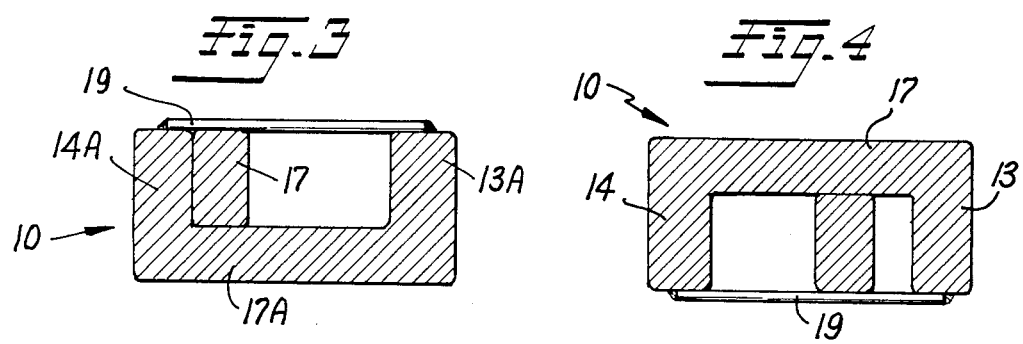
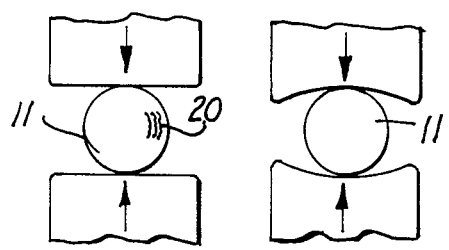
PRIOR ART
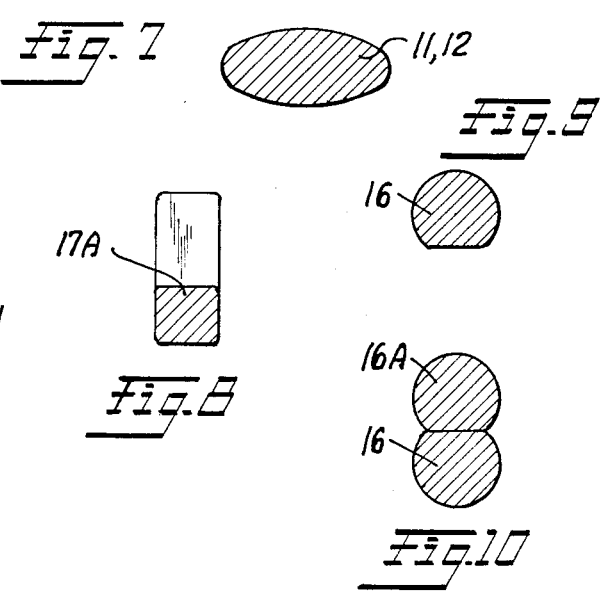

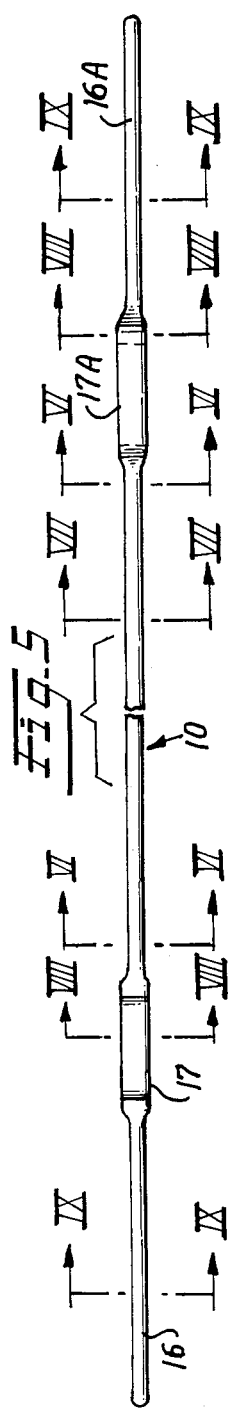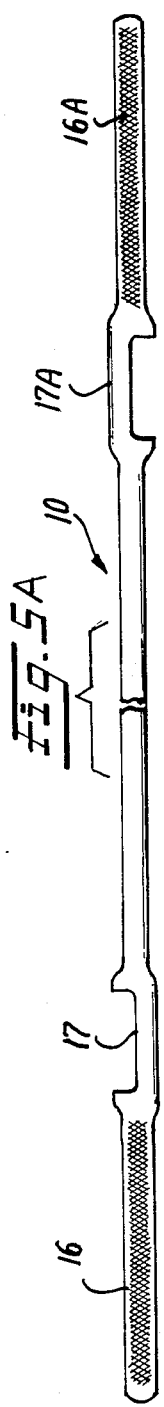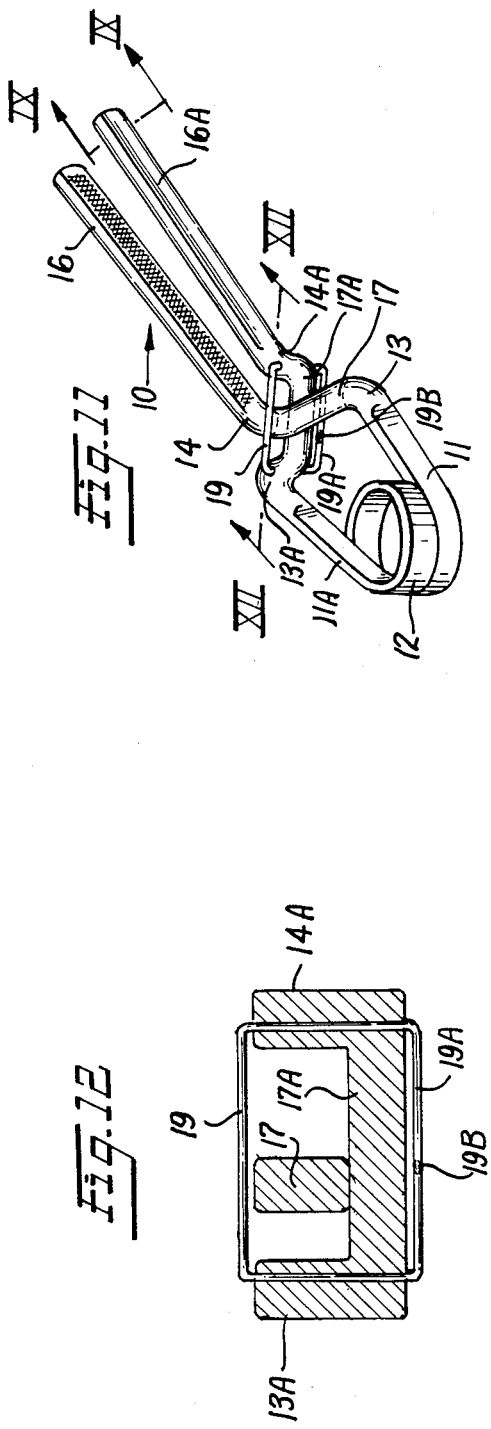

ANEURYSM CLIP

FIELD OF THE INVENTION

This invention relates to an improved aneurysm clip (clamp) for permanently or temporarily isolating an aneurysm from the artery to which it is attached.

BACKGROUND PROBLEM AND PRIOR ART

A cerebral aneurysm clip (clamp) is a surgical instrument for clamping the base part of a cerebral aneurysm to either temporarily or permanently isolate the latter from the cerebral artery. For this purpose, the aneurysm clip must be able to maintain the clamping pressure with high reliability as long as desired without causing injury to the wall of the blood vessel to which it is attached. Such injury could be caused by shearing action resulting from improper alignment of the jaws of the clip, or by improper magnitude of pressure, or by introduction of foreign material trapped in the cracks and crevices of a poorly constructed clip, or by the electromagnetic properties of clips made of improperly chosen materials used in their construction. There are a number of different kinds of cerebral aneurysm clips available in the art today; however, these are made of improperly chosen materials which interfere with important diagnostic techniques such as magnetic resonance imaging (MRI or NMR) due to haloing caused by the magnetic materials.

In order to provide satisfactory and prolonged service when properly implanted, a cerebral aneurysm clip must satisfy the following criteria;

1. The clamping pressure of the jaws of the clip must be sufficient for isolating a cerebral aneurysm, but not so great that it could damage the wall of the blood vessel to which it is attached whether used in a permanent implant or in a temporary implant application mode.

2. The clamping pressure of the clip must not change with time to prevent the clip from being displaced of slipping off.

3. Since aneurysm clips are often left permanently in the brain, the size of the clip must be as small as possible and it should not be made of ferromagnetic materials or materials which cause haloing in magnetic resonance imaging.

4. The shape of the clip should be such that the surgeon who is using it in an implant can view it clearly at all times without his view being obstructed during the implant operation.

5. To prevent unintentional tears and pressure points, jagged edges must be absent from the exterior surface of the clip.

6. Cracks in the exterior surface of the clip, even extremely fine micro-cracks, crevices and other similar defects should be absent from the surface of the clip in order to reduce the possibility of trapping foreign matter and contamination.

7. In order to prevent scissoring of the vessel wall to which the clip is attached, it is imperative that the jaws of the clip be properly aligned at all times both in its opened and closed state.

8. It is highly desirable, if not imperative, for the surgeon implanting the clip to be able to easily distinguish between seemingly identical clips sizewise which have different ranges of closing force, a requirement largely used to distinguish between temporary and permanent implants.

A basic aneurysm clip having no provision for maintaining jaw alignment, such as is described in U.S. Pat. No. 3,827,438, issued Aug. 6, 1974, or U.S. Pat. No. 4,024,868, issued May 24, 1977, would not be acceptable for implant purposes under the above-noted criteria.

A number of aneurysm clips having differently designed jaw guides for keeping the clamping jaws properly aligned have been proposed and are available. The simplest aneurysm cllips with provision for maintaining jaw alignment resemble electrical clamps where a window is provided in one arm to confine the movement of the second arm. Such a clamp is described in U.S. Pat. No. 4,484,581 issued Nov. 27, 1984. Aneurysm clips of this type usually are made of rather wide strips of material which unfortunately obstruct the view of the surgeon implanting the device. Furthermore, the width of the jaws prevents precision clamping of the narrow aneurysm base. Where the dimensions of this type of known clip are reduced to dimensions more typical in cerebral implants (a few millimeters to 1–2 centimeters), this known type of clip must be made of stainless steel to provide adequate strength in the "window frame" and in the thin arm portion which glides inside the frame. The variation of this type of "window frame" alignment is a partial window frame enclosed by a wide bridging member welded in place over the partial window as described in the above-noted U.S. Pat. No. 4,484,581.

U.S. Pat. No. 4,192,315, issued Mar. 11, 1980 discloses an aneurysm clip in which the clamping ends of the clip are supported by cross arms which cross inside the annulus of a ring loop. The disadvantage of this design is the presence of the protruding, loose loop, which if tightened would interfere with the smooth movement of the clamping jaws. U.S. Pat. No. 3,598,125 is another example of a clip having too much bulk and exterior protuberants for safe implantation in humans.

Another known aneurysm clip is described in U.S. Pat. No. 4,360.023, issued Nov. 23, 1982. This known clip uses a metal guide wire consisting of two leg portions and a straight guide portion which bridges the crossing region of the cross arms that support the clamping jaws of the clip. The disadvantage of this construction becomes immediately apparent when the clips are viewed at 50 times or higher magnification. Holes are drilled through the two arm portions in which the leg portions of the guide wire are mounted and then the leg portions are riveted into the holes for securely imbedding and fixing the straight guide portions into bridging relationship over the crossing arm portions. Unacceptable microcracks, voids and crevices are produced and are clearly visible on both sides of the two cross arms. Furthermore, micro-cracks are formed and clearly visible on the two clamping arm portions of the clip. The clips which have been examined were made out of chrome-cobalt alloy steel. Defects such as those mentioned above would be even more pronounced and dangerous if titanium or titanium alloys were used to fabricate the design, because titanium is prone to embrittlement and micro-cracking. At the same time, titanium and some titanium alloys (e.g. 6-4 alloys) are most desirable for implants since they are inert, compatible with body fluids, are non-magnetic and do not produce MRI haloes.

Currently, some of the known aneurysm clips are color coded. Since the temporary clips generally have closing forces in the 40-80 grams range, while the clips to be permanently implanted have closing forces in the 110-150 grams range, the temporary clips often are color coded for easy identification. This coloring customarily is done by the application of yellow electroplated gold to the clamping arms portion. However, any electroplating operation presents an inherent danger of peeling due to poor adhesion. This well known fact is aggravated by the further fact that chrome-cobalt alloys and similar steel alloys are notoriously difficult to activate for electroplating. Furthermore, dissimilar metals are susceptible to galvanic corrosion. Since voids, crevices, cracks and the like entrap electrolytes used in coloring the metals, the requirement for absence of surface imperfections is even more stringent for clips which are color coded in this manner.

SUMMARY OF INVENTION

It is a primary object of this invention to provide an improved cerebral aneurysm clip which satisfies the above-described criteria fully and yet is free from the above discussed problems encountered with prior art aneurysm clips intended for the same purpose.

Another object of the invention is to provide an improved cerebral aneurysm clip made entirely out of titanium or a titanium alloy.

An additional object of the invention is to provide improved cerebral aneurysm clips which can be readily and inexpensively color coded as to the range of force and whether they are for temporary or permanent implant classification without the necessity of unacceptable gold plating or other coloring by use of dissimilar or other foreign coloring materials.

In practicing the invention, an aneurysm clip is provided which comprises two clamping arms formed on the respective free ends of an elongated, continuous resilient member formed from material that is compatible with human tissue and nonmagnetic. The elongated resilient member is coiled in an intermediate section thereof to form coil spring means for normally urging the clamping arms together in a resilient manner. The elongated resilient member is further shaped to form two forearm sections extending outwardly and away from the coiled spring means in the direction of the clamping arms with the forearm sections terminating in inwardly bent first elbow portions that support respective cross arm sections. The cross arm sections extend from the respective first elbow portions in mutually crossing and slidably engaging relationship with each other and terminate in second inwardly bent elbow portions that support the respective clamping arm sections of the aneurysm clip. At least one of the cross arm sections has a U-shaped bend formed therein of sufficient width and depth to form a retaining guide means that slidably accommodates the remaining cross arm section of the clip. A straight wire-like retaining member likewise of human tissue compatible material is secured lengthwise over the said one cross arm section at each side of the U-shaped bend formed therein and bridges the U-shaped bend so as to lie in a plane spaced from and substantially parallel to the bottom of the U-shaped bend. In this construction the straight wire-like retaining member applies transversely directed force to the cross arm sections in the region of crossing to thereby urge the two cross arms and respective clamping arm sections thereof together in a direction at right angles to the plane of movement of the clamping arms.

In preferred embodiments of the invention an aneurysm clip is provided having the above set forth structural features and wherein complementary U-shaped bends are formed in each of the cross arm sections of the clip and at least one straight wire-like retaining member bridges the U-shaped bend in one of the cross arm sections. The clips preferably are made of titanium of titanium alloy material and are color coded with interference colors produced by anodic oxidation of the titanium or titanium alloy.

In a particularly preferred construction of an aneurysm clip according to the invention, the straight wire-like retaining member comprises one side of a closed loop formed by a single elongated wire-like retaining member having the respective ends thereof threaded through small openings formed through at least one arm section having a U-shaped bend therein at points near the first and second elbow portions on respective sides of the U-shaped bend. The ends of the wire-like member are joined together by welding to result in a tightly fitted loop embracing both cross arm sections in the crossing region and restricting lateral movement therebetween. As a result, the welding operation required to secure the loop in place on the clip is performed only on the ends of the elongated wire-like retaining member without requiring that the main body of the aneurysm clip be elevated to welding temperature at any point on its surface. Consequently, the original metallurgical properties and smoothness of the surface of the clip itself are unimpaired by the welding operation. The further anodic oxidation of the clip after assembly further insures the existence of a smooth outer surface without surface imperfections.

BRIEF DESCRIPTION OF DRAWINGS

These and other objects, features and many of the attendant advantages of this invention will be appreciated more readily as the same becomes better understood from a reading of the following detailed description, when considered in connection with the accompanying drawings, wherein like parts in each of the several figures are identified by the same reference characters, and wherein:

FIG. 1 is a perspective view illustrating a cerebral aneurysm clip constructed according to the invention;

FIG. 2 is a top plan view illustrating the cerebral aneurysm clip shown in FIG. 1;

FIG. 3 is a cross sectional view taken along the line III—III in FIG. 2;

FIG. 4 is a cross sectional view similar to FIG. 3 of an alternative embodiment of the aneurysm clip shown in FIGS. 1 and 3;

FIG. 5 is a top plan view of an elongated continuous resilient member formed from titanium or titanium alloy which is compatible with human tissue prior to being bent and shaped into the aneurysm clip shown in FIG. 1 or FIG. 11;

FIG. 5A is a side view of the elongated resilient member shown in FIG. 5;

FIG. 6 is a cross sectional view taken along the line VI—VI in FIG. 2 and FIG. 5;

FIG. 7 is a cross sectional view taken along the line VII—VII in FIG. 2 and in FIG. 5;

FIGS. 7A and 7B illustrate a prior art and a preferred coining operation used in practicing the invention;

FIG. 8 is a cross sectional view taken along the line VIII—VIII in FIG. 2 and FIG. 5;

FIG. 9 is a cross sectional view taken along the line IX—IX in FIG. 1 and in FIG. 5;

FIG. 10 is a cross sectional view taken along the line X—X in FIG. 2;

FIG. 11 is a perspective view of a different and preferred cerebral aneurysm clip constructed according to the invention and which uses the same elongated, resilient type titanium or titanium alloy body member shown in FIGS. 5 and 5A which was used to fabricate the embodiment of the invention shown in FIG. 1; and FIG. 12 is a cross sectional view taken along the line XII—XII of FIG. 11.

BEST MODE OF PRACTICING INVENTION

The cerebral aneurysm clip (or clamp) constructed according to the invention, is formed by bending a continuous, elongated, resilient member 10 (shown in FIGS. 5 and 5A) fabricated from titanium metal or a titanium alloy such as titanium 6–4 alloy composed of 6 parts aluminum, 4 parts vanadium and the remainder titanium. The titanium alloy is a suitable material since it is inert, compatible with human body fluid and tissue, non-magnetic, and has been approved by the FDA for use in human implants. The aneurysm clip is formed by first stamping (coining) elongated resilient member 10 shown in FIGS. 5 and 5A from a solid rod of titanium or titanium alloy having, for example, a diameter of about 35 mils (35 milliinches) and a length of about 2 inches. It should be noted that these particular parameters for the novel aneurysm clip here described are exemplary only for the invention is in no way limited to fabrication of clips in this particular size range. The coining is done with coining dies as illustrated in FIGS. 7A and 7B to provide the rod at different sections along its length with desired cross-sectional configurations and dimensions at the respective sections in question. This operation, referred to as a coining operation, may be carried out with a single elongated coining die whose segments may be differently configured at different sections along its length in order to provide the required cross-sectional configurations and dimensions for the respective sections of the finished elongated member 10 shown in FIGS. 5 and 5A. With such a die a single coining operation is sufficient to accomplish the required shaping and sizing of the blank starting rod along its length. Alternatively, multiple, separate coining operations may be carried out on the starting rod at the different sections along its length to achieve the same end result.

The desirability of using the very biocompatible, alpha-beta titanium alloys, such as the titanium 6–4 alloy, for permanent implant aneurysm clips has been widely acknowledged in the medical literature and has been approved by the FDA for implants in human beings. The great difficulty in forming such alloys prevented their use in aneurysm clips heretofore. The name alpha-beta alloys denotes the presence of two distinct crystallographic phases: close-packed hexagonal and body-centered cubic structures together with controlled amounts of stabilizing alloying elements. Due to the presence of the two phases, such alloys are notch-sensitive, meaning a tendency for surface imperfections to propagate as cracks. Cracks are likely to develop during compressive deformation, such as occur during the coining and coiling of the spring section 12 of an aneurysm clip such as shown in FIG. 1, where the thickness of the round starting rod must be reduced by close to 50% for proper spring action. It was found that even fully annealed alpha-beta alloy starting rods tend to develop unacceptable longitudinal cracks such as shown at 20 in FIG. 7A at less than 20% reduction in diameter while using conventional coining dies having a flat surface as shown in FIG. 7A. Stress analysis revealed that these cracks are due to elastic buckling when coiled, which causes failure in lateral shear.

It was discovered that the use of concave coining dies as shown in FIG. 7B were very effective buckling restraints and prevented shears and therefore the development of cracks during subsequent coiling. Such a concave coining die distributes the load and prevents lateral shear while flowing the metal. Approximately 50% reductions in the diameter of the titanium alloy starting rod from 35 mils down to 20–25 mils could be obtained in a room temperature coining operation without the development of cracks. The slope of the concave die surface depends on the desired percentage of deformation and it can be calculated by someone skilled in the art of stress analysis.

Additionally, it was found that by heating the dies to a moderate temperature, considerably greater deformation of the titanium starting rod could be achieved before cracks developed. Thus, titanium and titanium alloy parts maintained at 600–700 degrees Fahrenheit permitted approximately 40% reduction in the starting rod diameter even without the use of concave dies. For alpha-beta titanium alloys, the beta phase transitus temperature sets a practical upper limit to heating, and it was found that approximately 800 degrees Fahrenheit was the maximum advisable temperature for coining such alloys.

Combination of both heating the starting rod and use of concave coining dies resulted in spring coil 12 portions (sections) having a substantially flattened oval configuration as shown in FIG. 7 which were not only free of cracks but also sufficiently free of undesirable residual stresses. After elongate member 10 has been sized and shaped in the above briefly described manner, it is rotated 90 degrees about it's longitudinal axis from the position shown in FIG. 5 to that shown in FIG. 5A. The first U-shaped bend 17 is formed to a depth of about 10 mils leaving the section 17 with a shortest cross-sectional dimension of about 25 mils. The elongate member 10 then is rotated 180 degrees from the position shown in FIG. 5A and an identical, second U-shaped bend 17A then is stamped into the opposite end of member 10 to result in the structure shown in FIGS. 5 and 5A.

It should be noted at this point in the description that only the spring portion 12 of the aneurysm clip requires the special coining operation described briefly above. The remaining portions or sections of the starting rod to be shaped in order to complete the elongated member 10 shown in FIGS. 5 and 5A do not require as much deformation as the coil portion 12 and are not stressed by coiling in the same manner, and hence can be shaped and dimensioned with conventional coining operations using dies such as shown in FIG. 7A.

The elongated resilient metal member 10 having the configuration shown in FIGS. 5 and 5A is then bent and shaped as best seen in FIG. 1 of the drawings so as to form a centrally located coil portion 12 that terminates in two outwardly extending forearm sections 11 and 11A. The forearm sections 11, 11A extend outwardly and away from the coil portion 12 in the direction of the respective free clamping end sections 16 and 16A of the clip that have a minimum in cross-sectional dimension of 30 mils in the example cited and planar surfaces in mutual abutting clamping contact as shown in FIG. 10 of the drawings. The forearm sections 11, 11A of the clip terminate in inwardly bent elbow portions 13, 13A from which cross arm sections 17 and 17A of the clip extend. The remote ends of the cross arm sections 17 and 17A terminate in second inwardly bent elbow portions 14, 14A respectively, which in turn support the respective clamping arms 16 and 16A of the clip.

In the embodiment of the invention shown in FIG. 1, if desired, only the cross arm section 17A or 17 may be provided with a U-shaped bend as shown in FIG. 3 of FIG. 4 and the remaining cross arm section 17 or 17A left straight. Preferably, however, both cross arm sections 17 and 17A are provided with U-shaped bends as illustrated in FIGS. 5 and 5A in a complimentary and slidably engaging manner. The coil 12 is formed by winding elongated member 12 about a mandrel to form the coil portion 12 at or near a central intermediate part of elongated resilient member 10. This coil gives resiliency to the clip and causes the clipping arms 16 and 16A to normally close on themselves as shown in FIG. 2 of the drawings. The two forearm sections 11 and 11A extending outwardly from coil 12 are oval in cross-section similar to the turns of coil 12 as shown in FIG. 7 of the drawings and are bent inwardly at equidistant points from the coil 2 to form the first elbows 13 and 13A. The cross arm sections 17 and 17A, respectively, extend from the first elbows 13 and 13A which are circular in cross-section as shown in FIG. 6.

The cross arm sections 17 and 17A mutually cross each other at a crossing region located intermediate the length of the two sections and also slidably engage each other at the crossing region. The cross arm sections 17 and 17A terminate in second elbow portions 14 and 14A which are circular in cross-section as shown in FIG. 6 and are bent inwardly and support the clamping arm sections 16 and 16A in a normally closed, clamping condition as shown in FIG. 2 and FIG. 10 of the drawings. If desired, only one of the cross arm sections such as 17A can be bent into a U-shape along its length as illustrated in FIG. 3, for example. FIG. 3 is a cross sectional view taken through plane III—III of FIG. 2 and clearly illustrates the relationship of the two cross arm sections 17 and 17A in the crossing region. As noted earlier, only one of the cross arm sections, such as 17A, can have the U-shaped bend formed therein with the remaining cross arm section 17 being straight. In this eventuality, then the U-shaped bend in 17A must be deep enough to accommodate the full cross sectional dimension of the cross arm section 17. Alternatively, and preferably, both cross arm sections 17 and 17A have U-shaped bends formed therein in the crossing region as illustrated in FIGS. 3 and 4 as well as 5 and 5A of the drawings considered together. In this eventuality, the U-shaped bands in each cross arm section 17 and 17A need only be deep enough to accommodate half the cross sectioned dimension of the opposite cross arm section. This preferred construction is illustrated in FIG. 5A of the drawings. By using this preferred configuration less stressing of the metal of member 10 is required in order to shape the desired U-bends in the cross arm sections of the clip.

A straight wire-like retaining member 19 also is provided (as best seen in FIG. 3) which is fabricated from the same material, such as titanium or titanium alloy. As shown in FIGS. 1-3, the straight wire-like retaining member 19 is secured lengthwise along the cross arm section 17A and spot welded to the top of the respective first amd second elbow portions 13A and 14A so that it bridges the U-shaped bend in cross arm section 17A and lies in the plane spaced from and substantially parallel to the bottom of the U-shaped bend. The opposite cross arm section 17 extends in mutually crossing and slidably engaging relationship with the upper surface of the U-shaped bend in cross arm section 17A and is retained within the space defined by the U-shaped bend in cross arm section 17A by the straight wire-like retaining member 19. By this construction the straight wire-like retaining member 19 applies orthogonally directed restraining force to the cross arm sections 17 and 17A within the region of crossing to thereby urge the two cross arm sections and their respective clamping arms 16 and 16A together in a direction at right angles to the plane of movement of the clamping arms.

FIG. 4 depicts an alternative construction for use in those embodiments of the invention wherein both cross arm sections 17 and 17A have U-shaped bends formed therein as illustrated in FIG. 5A. In aneurysm clips constructed in this manner, if desired, a second straight, wire-like retaining member 19A of identical construction to the retaining member 19 described with relation to FIG. 3, can be bridged across the U-shaped bend formed in the cross arm section 17 in the manner shown in FIG. 4. The additional straight, wire-like retaining member 19A may be considered redundant; however, because of the critical nature of the use of the aneurysm clip, the extra strength and assurance provided by its presence to prevent lateral displacement of the clamping arms 16 and 16A relative to each other may be justified.

FIGS. 11 and 12 of the drawings illustrate still another, and most preferred, embodiment of the invention. This embodiment of the invention is fabricated from an elongated, continuous, resilient titanium or titanium alloy member 10 such as that illustrated in FIGS. 5 and 5A of the drawings and shaped in the same manner described with relation to FIGS. 1 and 2 to provide an improved cerebral aneurysm clip. In the embodiment of the invention shown in FIGS. 11 and 12, the straight wire-like retaining member 19 comprises one side of a closed loop formed by a single, elongated, straight wire-like retaining member having the respective ends thereof threaded through small openings drilled or otherwise formed through the elbow portions 13A and 14A disposed on each side of the U-shaped bend in cross arm section 17A on respective sides of the U-shaped bend in cross arm 17A. The ends of the wire on the opposite side are bent over to form a closed loop and spot welded together at a point 19B to thereby form first and second straight wire-like retaining members 19 and 19A. This construction results in a tightly fitted loop which embraces the U-shaped bends in both cross arm sections 17 and 17A in the crossing region and prevents vertical movement between the cross arm sections 17, 17A and their corresponding clamping arm sections 16 and 16A.

It should be noted at this point in the description that the embodiment of the invention shown in FIGS. 11 and 12 requires that a welding operation be made only with respect to the ends of the looped straight wire-like retaining member 19, 19A with the loop in place, but does not require that the main body on the aneurysm clip be elevated to welding temperatures at any points along its surface as would be required in the embodiments shown in FIGS. 1-4. Additionally, the loop provided in the embodiment of the invention shown in FIGS. 11 and 12 provides an additional safety factor insofar as the retaining guide wires 19 and 19A would be retained in place even in the unlikely event of the failure of the weld 19B.

It should be further observed with regard to all embodiments of the invention disclosed that the U-shaped bends in cross arm sections 17 and 17A are formed with flat surfaces to provide better sliding action at the cross over region. It will be understood that when the forearm sections 11 and 11A of the clip are squeezed toward each other (by a suitable tool not shown) the clamping jaws 16 and 16A will be moved apart so that the clip assumes the open state shown in FIG. 1 and FIG. 11, for example. When the force is removed, the clip will resume the closed state shown in FIG. 2 with the clamping jaws in mutual abutting and clamping relationship for clamping an object therebetween. During operation of the clip, if the jaws 16 and 16A were brought to a closed condition in a state where they were incorrectly opposed to each other, the clamping force of the clip would be reduced and shearing action could result when it has an object clamped between the two clamping jaws. In order to prevent this from happening, the guide wires 19 and/or 19A made of the same metal or alloy as the clip, is secured across the U-shaped bend 17, 17A thereby preventing the opposed cross arm sections 17A, 17 from leaving the mutually enclosing and restraining U-shaped bend in the opposite cross arm section.

The straight, wire-like retaining members 19 and 19A are not obstructive to the relative sliding movement between the cross arm sections 17 and 17A and are designed so that the guide wire 19 presses U-shaped cross arm section 17 against the U-shaped bend in cross arm section 17A (or vice versa) to keep the two cross arm sections in tight sliding contact with each other. Since the straight, wire-like guide member 19 and/or 19A extends over the distance through which the cross arm sections slidingly move within the complementary U-shaped bend of the opposite cross arm (when the forearm sections 11, 11A are squeezed together) the pressing force by the guide wire member 19, 19A is imparted over the entire operating range of the clip. Thus, correct opposing abutment between the clamping jaws 16 and 16A always is maintained and correct clamping operation of the aneurysm clip is assured at all times.

It is believed evident to one skilled in the art of manufacture of aneurysm clips, that the physical dimensions of aneurysm clips constructed according to the invention, and the shape of the clamping jaws can easily be modified to produce clips in the full size and shape ranges used for cerebral aneurysm clips. In some of these aneurysm clips, the clamping jaws 16 and 16A are straight. In others they may be bent at various angles and degrees of curvatures. Changes in the shapes and sizes of the jaw portions 16 and 16A are believed to be obvious to one skilled in the art in the light of the teachings of the present invention.

Aneurysm clips made of titanium or titanium alloy according to this invention can easily be color coded without the need to resort to electroplating. Titanium and titanium alloys acquire their great inertness in the presence of a thin passivating oxide film on the surface. Such passivating oxide films can also be grown by various surface oxidation techniques, such as heating the titanium or titanium alloy in air or oxygen to elevated temperatures. Heating the titanium or titanium alloys at the elevated temperatures can have the disadvantage of influencing the metallurgical temper of the metal or alloy. A more convenient and controllable oxidation technique is electrolytic oxidation. Electrolytic oxidation can produce oxide film thicknesses exceeding the thicknesses produced by spontaneous air oxidation at ambient or elevated temperatures. Thus, if the titanium or titanium alloy fabricated aneurysm clips are immersed in suitable electrolytic solutions of oxidizing acids under anodic conditions, oxide film thicknesses in excess of several wavelengths of green light can be rapidly grown.

Of particular interest are fractional wavelength interference color surfaces grown in dilute solutions of nitric acid at room temperature. Depending upon the applied anodic voltage, the whole spectrum of interference colors can be obtained on the surface of the titanium and its alloys in minutes. Danger of anodic corrosion and breakdown is virtually absent as long as the voltage is kept below about 10 volts. The resulting oxide films, and therefore the resulting colored surfaces, are tenaciously adherent. There is little or no danger of accelerated galvanic corrosion in such structures and in fact is completely absent. This is in contrast to the pronounced tendency to galvanic corrosion of the gold plated surfaces of prior known aneurysm clips. The high degree of inertness of the titanium and its alloys is maintained by treatment in this manner and any residual nitric acid is easily rinsed off, or if desired it is driven off in a low temperature bake. Yellows and blues are the most readily reproduced colors using this technique. Further, the passivating oxide surfaces resulting from the treatment can in effect coat and close any micro-fissures that might have been developed in the surface of the titanium during earlier fabrication steps of the aneurysm clip. Thus, not only can highly desirable and reliable color coding be achieved, but the resulting finish provides a smooth surface for the clip which is not subject to catching and holding foreign matter in the form of blood or tissue.

From the foregoing description, it will be appreciated that aneurysm clips made possible by the present invention are more reliable and desirable than any of the known prior art clips. Their construction does not require riveting or other similar operations of restraint members onto the clip and therefore it does not tend to result in crevices, voids or micro-cracks such as can be found in clips made according to the teachings of U.S. Pat. No. 4,360,023. In the particularly preferred embodiment of the invention, welding onto the main body of the clip is not required with the inherent danger of altering the temperature induced physical characteristics of the clip. In contrast to the prior art clip disclosed in U.S. Pat. No. 4,484,581, the cross arm sections 17 and 17A are left with their original circular cross sectional thickness by eliminating the requirement for drastically reducing the thickness of at least one of the arms at the cross over region as is true of other aneurysm clips which provide lateral alignment guides. On the other hand, if flattened sliding surfaces are desired as described with relation to FIG. 9 (for example) such flattening can be achieved with a minor coining operation which does not remove material and does not affect to any significant degree the cross sectional area or the width of the cross arms. The cross sectional area of the different sections and portions of the clip remains essentially uniform everywhere in the clip. This permits the use of the smallest wire diameter as determined by bending moment calculations alone and not by secondary considerations. The weight and size of the clip can thus be held to a minimum for any desired force range.

Surface metal joining techiques applicable to titanium and its alloys can be used for the attachment of the straight wire-like guide member or the welding together of the two ends of the guide wire loop. Of particular importance is the applicability of such techniques as electron beam welding and spot and flash welding for titanium and titanium alloys. The capability of color coding the assembled clips by a simple electrolytic bath treatment that results in a superior color coding adds greatly to the safety and utility of aneurysm clips constructed according to the invention.

MEDICAL SERVICE APPLICATION

The invention comprises an improved cerebral aneurysm clip for use as a surgical instrument in clamping the base part of a cerebral aneurysm to either temporarily or permanently isolate the aneurysm from the cerebral artery.

Having described several embodiments of a new and improved cerebral aneurysm clip constructed according to the invention, it is believed obvious that other modifications and variations of the invention will be suggested to those skilled in the art in the light of the above teachings. It is therefore to be understood that changes may be made in the particular embodiments of the invention described which are within the full intended scope of the invention as defined by the appended claims.

What is claimed is:

1. An aneurysm clip comprising two clamping arms formed on the respective free ends of an elongated continuous resilient member formed from tittanium-like material that is compatible with human tissue, and non-magnetic, said elongated resilient member being coiled in an intermediate section thereof to form coil spring means for normally urging the clamping arms together in a resilient manner, the elongated resilient member being further shaped to form two forearm sections extending outwardly and away from the coil spring means in the direction of the clamping arms with the forearm sections terminating in inwardly bent first elbow portions that support respective cross arm sections, the cross arm sections extend from the respective first elbow portions in mutually crossing and slidably engaging relationship with each other and terminate in second inwardly bent elbow portions that support the respective clamping arms of the aneurysm clip, at least one of said cross arm sections having a separately defined U-shaped bend therein of sufficient width and depth to slidably accommodate the remaining cross arm section, the depth of the U-shaped bend being at least equal to the thickness of the remaining cross arm section slidably supported within said U-shaped bend and the two cross arm sections having substantially the same cross-sectional area as the original starting material from which the clip is formed, and a straight wire-like retaining member likewise of human tissue compatible material secured lengthwise over said at least one cross arm section at each side of the U-shaped bend and bridging the U-shaped bend so as to lie in a plane spaced from and substantially parallel to the bottom of the U-shaped bend whereby the straight wire-like retaining member applies orthogonally directed force to the cross arm sections in the region of crossing to thereby urge the two cross arms and the respective clamping arms together in a direction at right angles to the plane of movement of the clamping arms.

2. An aneurysm clip according to claim 1 wherein complementary U-shaped bends are formed in each of the cross arm sections of the clip at a lesser depth than if only one cross arm section has a U-shaped bend formed therein and at least one straight wire-like retaining member bridges the U-shaped bend in one of the cross arm sections.

3. An aneurysm clip according to claim 1 wherein the clip is color coded with interference colors produced by anodic oxidation of the titanium.

4. An aneurysm clip according to claim 2 wherein the clip is color coded with interference colors produced by anodic oxidation of the titanium alloy.

5. An aneurysm clip according to claim 1 wherein the straight wire-like retaining member comprises one side of a closed loop formed by a single elongated wire-like retaining member having the respective ends thereof threaded through small openings formed through the said one arm section having the U-shaped bend therein at points near the first and second elbow portions on respective sides of the U-shaped bend with the ends of the wire-like member being bent towards each other and joined together by welding to result in a tightly fitted loop embracing both cross arm sections in the crossing region and restricting lateral movement therebetween whereby the welding operation required to secure the loop in place on the clip is performed only on the ends of the elongated wire-like retaining member without requiring that the main body of the aneurysm clip be elevated to welding temperature at any point on the surface to thereby maintain the metallurgical properties of the clip itself unimpaired by the welding operation.

6. An aneurysm clip according to claim 5 wherein the clip and wire-like retaining member are fabricated of titanium metal.

7. An aneurysm clip according to claim 5 wherein the clip and wire-like retaining member are fabricated from a titanium alloy.

8. An aneurysm clip according to claim 6 wherein the clip is color coded with interference colors produced by anodic oxidation of the titanium.

9. An aneurysm clip according to claim 7 wherein the clip is color coded with interference colors produced by anodic oxidation of the titanium alloy.

10. An aneurysm clip comprising two clamping arms formed on the respective free ends of an elongated continuous resilient member formed from material that is compatible with human tissue, and non-magnetic, said elongated resilient member being coiled in an intermediate section thereof to form coil spring means for normally urging the clamping arms together in a resilient manner, the elongated resilient member being further shaped to form two forearm sections extending outwardly and away from the coil spring means in the direction of the clamping arms with the forearm sections terminating in inwardly bent first elbow portions that support respective cross arm sections, the cross arm sections extend from the respective first elbow portions in mutually crossing and slidably engaging relationship with each other and terminate in second inwardly bent elbow portions that support the respective clamping arms of the aneurysm clip, at least one of said cross arm sections having a separately defined U-shaped bend therein of sufficient width and depth to slidably accommodate the remaining cross arm section, the depth of the U-shaped bend being at least equal to the thickness of the remaining cross arm section slidably supported within said U-shaped bend and the two cross arm sections having substantially the same cross-sectional area as the original starting material from which the clip is formed, and a straight wire-like retaining member likewise of human tissue compatible material secured lengthwise over said at least one cross arm section at each side of the U-shaped bend and bridging the U-shaped bend so as to lie in a plane spaced from and substantially parallel to the bottom of the U-shaped bend whereby the straight wire-like retaining member applies orthogonally directed force to the cross arm sections in the region of crossing to thereby urge the two cross arms and the respective clamping arms together in a direction at right angles to the plane of movement of the clamping arms, and wherein the straight wire-like retaining member comprises one side of a closed loop formed by a single elongated wire-like retaining member having the respective ends thereof threaded through small openings formed through the said one arm section having the U-shaped bend with the ends of the wire-like member being joined together by welding to result in a tightly fitted loop embracing both cross arm sections in the crossing region and restricting orthogonal movement therebetween whereby the welding operation required to secure the loop in place on the clip is performed only on the ends of the elongated wire-like retaining member without requiring that the main body of the aneurysm clip be elevated to welding temperature at any point on the surface to thereby maintain the metallurgical properties of the clip itself unimpaired by the welding operation.

11. An aneurysm clip according to claim 10 wherein complementary U-shaped bends are formed in each of the cross arm sections of the clip at a lesser depth than if only one cross arm section has a U-shaped bend formed therein and at least one straight wire-like retaining member bridges the U-shaped bend in one of the cross arm sections.

12. An aneurysm clip according to claim 10 wherein the clip is fabricated of titanium metal.

13. An aneurysm clip according to claim 10 wherein the clip is fabricated from a titanium alloy.

14. An aneurysm clip according to claim 12 wherein the clip is color coded with interference colors produced by anodic oxidation of the titanium.

15. An aneurysm claim according to claim 13 wherein the clip is color coded with interference colors produced by anodic oxidation of the titanium alloy.

16. An aneurysm clip according to claim 11 wherein the clip is fabricated of titanium metal.

17. An aneurysm clip according to claim 11, wherein the clip is fabricated from a titanium alloy.

18. An aneurysm clip according to claim 16, wherein the clip is color coded with interference colors produced by anodic oxidation of the titanium.

19. An aneurysm claim according to claim 18 wherein the clip is color coded with interference colors produced by anodic oxidation of the titanium alloy.

20. An aneurysm clip according to claim 10 wherein the intermediate section of the elongated resilient member that is coiled to form the coil spring means is formed by coining a starting rod of human tissue compatible and non-magnetic material or given length and cross-sectional diameter with a special coining operation using coining dies having confronting concave surfaces that embrace the diameter of the starting rod and under applied force cause the starting rod material to flow without fracture into a relatively flattened oval cross-sectional configuration having a lesser cross-sectional dimension of about half the cross-sectional diameter of the starting rod.

21. An aneurysm clip according to claim 10 wherein the intermediate section of the elongated resilient member that is coiled to form the coil spring means is formed by coining a starting rod of human tissue compatible and non-magnetic material of given length and cross-sectional diameter at an elevated temperature not in excess of 800 degrees Fahrenheit using conventional coining dies with opposed flat surfaces which under applied force to the starting rod to thereby cause the rod material to flow without fracture into a relatively flattened oval cross-sectional configuration having a lesser cross-sectional dimension of about half the cross-sectional diameter of the starting rod.

22. An aneurysm clip according to claim 10 wherein the intermediate section of the elongated resilient member that is coiled to form the coil spring means is formed by coining a starting rod of human tissue comatible and non-magnetic material or given length and cross-sectional diameter with a special coining operation using coining dies having confronting concave surfaces that embrace the diameter of the starting rod and applying force to the starting rod with the starting rod at an elevated temperature not in excess of 800 degrees Fahrenheit to thereby cause the rod material to flow without fracture into a relatively flattened oval cross-sectional configuration having a lesser cross-sectional dimension of about half the cross-sectional diameter of the starting rod.

23. An aneurysm clip according to claim 22 wherein the clip is fabricated of titanium metal.

24. An aneurysm clip according to claim 22 wherein the clip is fabricated from a titanium alloy.

25. An aneurysm clip according to claim 22 wherein complementary U-shaped bends are formed in each of the cross arm sections of the clip at a lesser depth than if only one cross arm section has a U-shaped bend formed therein and at least one straight wire-like retaining member bridges the U-shaped bend in one of the cross arm sections.

26. An aneurysm clip according to claim 25 wherein the clip is fabricated of titanium metal.

27. An aneurysm clip according to claim 25 wherein the clip is fabricated from a titanium alloy.

28. An aneurysm clip according to claim 26 wherein the clip is color coded with interference colors produced by anodic oxidation of the titanium.

29. An aneurysm clip according to claim 27 wherein the clip is color coded with interference colors produced by anodic oxidation of the titanium alloy.

* * * * *